United States Patent [19]
Treuner et al.

[11] 3,931,170
[45] Jan. 6, 1976

[54] 3-HETEROTHIO DERIVATIVES OF (CARBAMOYLTHIOACETYL)CEPHALOSPORINS

[75] Inventors: Uwe D. Treuner; Hermann Breuer, both of Regensburg, Germany

[73] Assignee: E. R. Squibb & Sons, Inc., Princeton, N.J.

[22] Filed: Aug. 30, 1974

[21] Appl. No.: 501,902

[52] U.S. Cl. .................. 260/243 C; 260/294.8 E; 260/332.2 A; 260/347.2; 260/455 A; 424/246
[51] Int. Cl.² ............... C07D 501/50; A61K 31/545
[58] Field of Search ................. 260/243 C

[56] References Cited
UNITED STATES PATENTS

| | | | |
|---|---|---|---|
| 3,391,141 | 7/1968 | Gottstein et al. | 260/243 C |
| 3,775,408 | 11/1973 | Ochiai et al. | 260/243 C |
| 3,812,116 | 5/1974 | Takano et al. | 260/243 C |

OTHER PUBLICATIONS
Gottstein et al., J. Med. Chem., 14, No. 8, pp. 770–772, (1971).

*Primary Examiner*—Nicholas S. Rizzo
*Assistant Examiner*—Diana G. Rivers
*Attorney, Agent, or Firm*—Lawrence S. Levinson; Merle J. Smith

[57] ABSTRACT

3-Heterothio(carbamoylthioacetyl)cephalosporin derivatives of the general formula

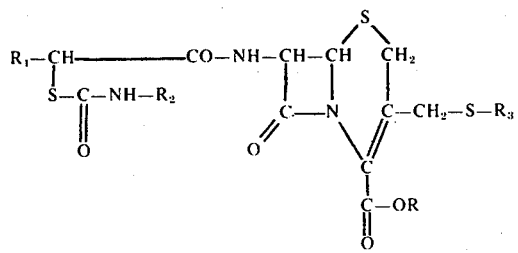

wherein R is hydrogen, lower alkyl, phenyl-lower alkyl, tri(lower alkyl)silyl, a salt forming ion or the group

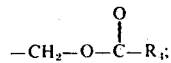

$R_1$ is hydrogen, lower alkyl, phenyl, thienyl, or pyridyl; $R_2$ is lower alkyl or phenyl-lower alkyl; $R_3$ is a five or six membered nitrogen, sulfur and/or oxygen containing ring system; and $R_4$ is lower alkyl, phenyl or phenyl-lower alkyl; are useful as antibacterial agents.

11 Claims, No Drawings

3-HETEROTHIO DERIVATIVES OF (CARBAMOYLTHIOACETYL)CEPHALOSPORINS

SUMMARY OF THE INVENTION

This invention relates to new 3-heterothio(carbamoylthioacetyl)cephalosporin derivatives of the formula (I)
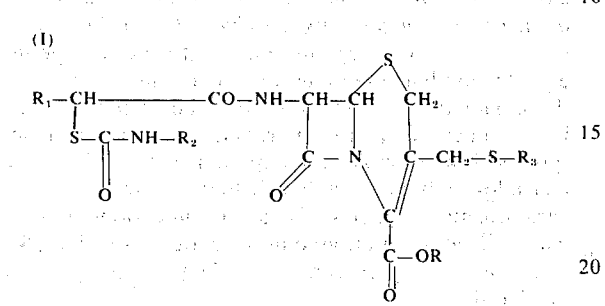

R represents hydrogen, lower alkyl, phenyl-lower alkyl, tri(lower alkyl)silyl, a salt forming ion or the group

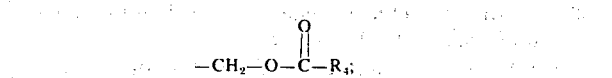

$R_1$ represents hydrogen, lower alkyl, phenyl, thienyl, or pyridyl; $R_2$ represents lower alkyl or phenyl-lower alkyl; $R_3$ represents a five or six-membered heterocycle including thiadiazole, oxadiazole, isoxazole, isothiazole, tetrazole, pyridine-N-oxide and their lower alkyl substituted analogs; $R_4$ represents lower alkyl, phenyl or phenyl-lower alkyl.

The preferred members within each group as as follows: R is hydrogen, alkali metal, trimethylsilyl, diphenylmethyl or

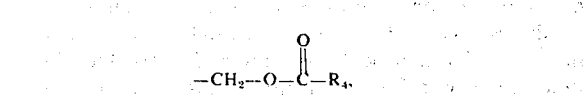

especially hydrogen, pivaloyloxymethyl, sodium or potassium; $R_1$ is hydrogen, phenyl or thienyl, especially hydrogen or phenyl; $R_2$ is lower alkyl, especially methyl or ethyl; $R_3$ is preferably (lower alkyl)-tetrazole or (lower alkyl)thiadiazole, especially wherein the lower alkyl group is methyl; $R_4$ is methyl or t-butyl.

DETAILED DESCRIPTION OF THE INVENTION

The various groups represented by the symbols have the meanings defined below and these definitions are retained throughout this specification.

The lower alkyl groups are the straight and branched chain hydrocarbon groups in the series from methyl to heptyl, the $C_1$ to $C_4$ members and especially methyl and ethyl being preferred.

The phenyl-lower alkyl radicals include a phenyl ring attached to a lower alkyl group of the kind described above as well as those containing two phenyl groups such as diphenylmethyl.

The salt forming ions represented by R are metal ions, e.g., alkali metal ions such as sodium or potassium, alkaline earth metal ions such as calcium or magnesium, or an amine salt ion, e.g., a (lower alkyl)amine like methylamine or triethylamine or a cycloalkylamine, like dicyclohexylamine, etc.

$R_3$ is thiadiazole, oxadiazole, isoxazole, isothiazole, tetrazole, pyridine-N-oxide and their lower alkyl substituted analogs, especially 1,3,4-thiadiazole, 1,2,4-thiadiazole, tetrazole, 5-methyl-1,3,4-thiadiazol-2-yl, 3-methyl-1,2,4-thiadiazol-5-yl, tetrazole and 1-methyltetrazol-5-yl.

The new cephalosporin derivatives of this invention are produced by several methods. According to one method, a 7-aminocephalosporanic acid (7-ACA) derivative of the formula (II)
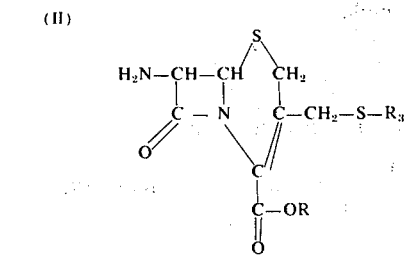

is reacted with a carbamoylacetic acid of the formula (III)
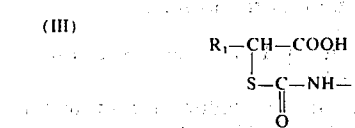

or an activated derivative of the former (II).

The activated derivatives referred to include, for example, the reaction product with an anhydride forming reagent such as ethylchloroformate, benzoyl chloride, pivaloyl chloride, etc., an acid chloride or an activated ester like the benzhydryl ester, t-butyl ester, trimethylsilyl ester or trimethylstannyl ester or triethylamine salt. Dicyclohexylcarbodiimide can also be used to effect the reaction.

One preferred synthesis comprises reacting the acid of formula III with the diphenylmethyl ester of the 7-ACA derivative of formula II and then hydrolyzing the ester with trifluoroacetic acid and anisole to obtain the free carboxyl group in the 4-position.

The reaction between the 7-aminocephalosporanic acid compound and the carbamoylacetic acid can be carried out, for example, by dissolving or suspending the acid in an inert organic solvent such as chloroform, tetrahydrofuran, methylene chloride, dioxane, benzene or the like, and adding, at a reduced temperature of about 0°–5°C, about an equimolar amount of the 7-ACA compound in the presence of an activating compound such as dicyclohexylcarbodiimide. The product of the reaction is then isolated by conventional procedures, e.g., by concentration or evaporation of the solvent. If a derivative of the 7-aminocephalosporanic acid compound, such as the diphenylmethyl ester is used, the free acid is obtained by hydrolysis, e.g., with trifluoroacetic acid or the like. Salts can then be derived from the free acid.

According to another preferred embodiment an acid of formula III is reacted with a compound of the formula (IV)

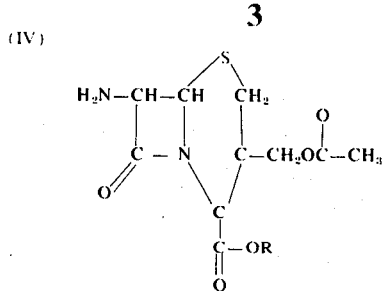

preferably wherein R is diphenylmethyl. When R is the preferred diphenylmethyl group, it is converted to the free acid with trifluoroacetic acid and anisole. The product of the formula (V)

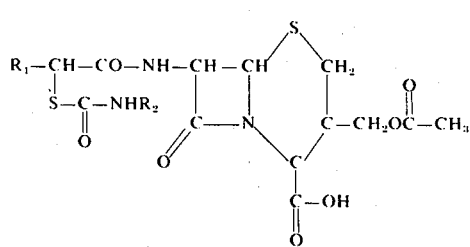

is then reacted with a thiol of the formula
(VI) $R_3$—SH
in basic solution, e.g., at a pH of about 7.8, to obtain the product of formula I.

Additional details of the procedure for producing compounds of formula III and V are found in our copending application Ser. No. 471,080, filed May 17, 1974.

When R is the acyloxymethyl group

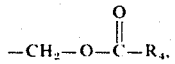

this group can be introduced into the 7-aminocephalosporanic acid moiety prior to the reaction with the carbamoylthioacetic acid or the activated derivative by treatment with one to two moles of a halomethyl ester of the formula
(VII) hal—$CH_2OCOR_4$
wherein hal is halogen, preferably chlorine or bromine, in an inert organic solvent such as dimethylformamide, acetone, dioxane, benzene or the like, at about ambient temperature or below.

The carbamoylacetic acid of formula III is produced by reacting a mercaptoacetic acid of the formula (VIII)

with a base, e.g., an alkylamine like triethylamine, and with an isocyanate $R_2N=C=O$, in an inert solvent like tetrahydrofuran, then acidifying, e.g., with hydrochloric acid or the like.

Alternatively the acid of formula V is converted to an ester like the diphenylmethyl or t-butyl ester by reaction with a diphenyldiazomethane or isobutylene, followed by reaction with the isocyanate and treatment with trifluoroacetic acid/anisole.

Further process details are also provided in the illustrative examples.

Certain of the compounds of this invention may exist in different optically active forms. The various stereoisomeric forms as well as the racemic mixtures are within the scope of the invention.

The compounds of this invention have a broad spectrum of antibacterial activity against both gram positive and gram negative organisms such as *Staphylococcus aureus, Salmonella schottmuelleri, Pseudomonas aeruginosa, Proteus vulgaris, Escherichia coli* and *Streptococcus pyogenes*. They are useful as antibacterial agents, e.g., to combat infections due to organisms such as those named above, and in general they can be utilized in a manner similar to cephradine and other cephalosporins. For example, a compound of formula I or a physiologically acceptable salt thereof can be used in various animal species affected by infections of such bacterial origin in an amount of about 1 to 75 mg/kg daily, orally or parenterally, in single or two to four divided doses.

Up to about 500 mg. of a compound of formula I or a physiologically acceptable salt thereof is administered by incorporating in an oral dosage form such as tablets, capsules or elixirs or in an injectable form in a sterile aqueous vehicle prepared according to conventional pharmaceutical practice.

The following examples are illustrative of the invention. All temperatures are in degrees celsius. Additional variations are produced in the same manner by appropriate substitution in the starting material.

EXAMPLE 1

DL-[[(Methylamino)carbonyl]thio]phenylacetic acid 10.08 g. (60 mM) of α-mercaptophenylacetic acid and 6.6 g. (60 mM) of triethylamine are dissolved in 50 ml. of tetrahydrofuran and 3.42 g. (60 mM) of methylisocyanate dissolved in 20 ml. of tetrahydrofuran are added dropwise with stirring. After stirring for 2 hours, the solvent is drawn off in a vacuum and the oily residue is dissolved in water. The mixture is then acidified with 2N hydrochloric acid and extracted three times each with 20 ml. of ether. After drying off the ether, 10.5 g. of white crystalline DL-[[(methylamino)-carbonyl]thio]phenylacetic acid are obtained, which is recrystallized from ether/petroleum ether, m.p. 128°–129°.

EXAMPLE 2

DL-[[(Ethylamino)carbonyl]thio]phenylacetic acid

By substituting ethylisocyanate for the methylisocyanate in the procedure of Example 1, white crystalline DL-[[(ethylamino)carbonyl]thio]phenylacetic acid is obtained and recrystallized from cyclohexane, m.p. 115°–117° (dec.).

EXAMPLE 3

DL-3-[(Acetyloxy)methyl]-7β-[[[[(methylamino)carbonyl]thio]-phenylacetyl]amino]-8-oxo-5-thia-1-azabicyclo[4.2.0]oct-2-ene-carboxylic acid, diphenylmethyl ester 1 g. (5 mM) of dicyclohexylcarbodiimide is added to 1.1 g. (5 mM) of DL-[[(methylamino)carbonyl]thio]-phenyl acetic acid in 50 ml. of tetrahydrofuran and stirred for 1 hour at −5°. 2.1 g. (5 mM) of 7-aminocephalosporanic acid, benzhydryl ester in 15 ml.

of tetrahydrofuran are then added and the mixture is stirred for 5 hours at 0° and for 1 hour at room temperature. The precipitate of dicyclohexylurea is filtered off and the filtrate is evaporated. The oily residue is dissolved in 20 ml. of methylene chloride. Filtration over charcoal and precipitation with petroleum ether produces 1.3 g. of white DL-3-[(acetyloxy)methyl-7β-[[[[(methylamino)carbonyl]thio]phenyl]acetyl]amino]-8-oxo-5-thia-1-azabicyclo[4.2.0]oct-2-ene-carboxylic acid, diphenylmethyl ester which is reprecipitated from methylene chloride/carbon tetrachloride, m.p. 73° (dec.).

EXAMPLE 4

DL-3-[(Acetyloxy)methyl]-7β-[[[[(methylamino)carbonyl]thio]-phenylacetyl]amino]-8-oxo-5-thia-1-azabicyclo[4.2.0]oct-2-ene-2-carboxylic acid 3 g. of the product of Example 3 are dissolved at 0° in 25 ml. of trifluoroacetic acid/anisole and stirred for 15 minutes. After drawing off the trifluoroacetic acid in vacuum, an oily residue remains which is washed repeatedly with absolute ether until it becomes quite firm. The residue is dissolved in sodium bicarbonate solution, filtered and acidified with hydrochloric acid, with cooling, to a pH of 2.5. The solution is extracted three times each with 20 ml. of ethyl acetate. The organic phase is dried and evaporated. 0.9 g. of DL-3-[(acetyloxy)methyl]-7β-[[[[(methylamino)carbonyl]-thio]phenylacetyl]amino]-8-oxo-5-thia-1-azabicyclo[4.2.0]oct-2-ene-2-carboxylic acid is obtained as a light yellow powder m.p. 121° (dec.) after reprecipitation from methylene chloride/petroleum ether.

EXAMPLE 5

Alternate method for producing the product of Example 4

4.5 g. (20 mM) of DL-[[(methylamino)carbonyl]thio]-phenylacetic acid are dissolved in 50 ml. of tetrahydrofuran. 2 g. (20 mM) of triethylamine are added and while stirring at a temperature of 0° 2.5 g. (20 mM) of ethyl chloroformate are added dropwise. After 1 hour, a solution of 5.4 g. (20 mM) of 7-aminocephalosporanic acid, triethylamine salt in 200 ml. of methylene chloride are added and the whole mixture is stirred for 14 hours at 5°. After filtering and drawing off the solvent, the oily residue is treated with water. The aqueous solution is extracted with ethyl acetate, filtered and acidified to pH 2.5. Repeated extraction with ethyl acetate and evaporation of the ethyl acetate solution in vacuum yields after recrystallization from methylene chloride/petroleum ether, DL-3-[(acetoxy)-methyl]-7β-[[[[(methylamino)carbonyl]thio]phenyl]amino]-8-oxo-5-thia-1-azabicyclo[4.2.0]-oct-2-ene-carboxylic acid as a light yellow powder, 2.5 g., m.p. 61°. The product produced by this method is only 67% pure.

EXAMPLE 6

DL-3-[(Acetyloxy)methyl]-7β-[[[[(ethylamino)carbonyl]thio]-phenylacetyl]amino]-8-oxo-5-thia-1-azabicyclo[4.2.0]oct-2-ene-2-carboxylic acid, diphenylmethyl ester 4.8 g. (20 mM) of DL-[[(ethylamino)carbonyl]thio]-phenylacetic acid are dissolved in 150 ml. of tetrahydrofuran and stirred with 8.4 g. (20 mM) of 7-ACA benzhydryl ester and 4.05 g. (20 mM) of dicyclohexylcarbodiimide for 8 hours at 20°. By evaporating the filtered solution, 9 g. of DL-3-[(acetyloxy)methyl]-7β-[[[[(ethylamino)carbonyl]thio]-phenylacetyl]amino]-8-oxo-5-thia-1-azabicyclo[4.2.0]oct-2-ene-2-carboxylic acid, diphenylmethyl ester are obtained as a yellow powder, m.p. 75° (dec.).

EXAMPLE 7

3-[[(5-methyl-1,3,4-thiadiazol-2-yl)thio]methyl]-7-amino-8-oxo-5-thia-1-azabicyclo[4.2.0]oct-2-ene-2-carboxylic acid A mixture of 13.6 g. (0.5 M) of 7-aminocephalosporanic acid (7-ACA) in 100 ml. of water and 50 ml. of acetone are brought to pH 8 with sodium hydroxide while stirring. 9.8 g. (0.57 M) of 2-methyl-1,3,4-thiadiazole-5-thiol are added and the mixture is heated at 80° for 4 hours. After cooling to 5°, this is acidified to pH 3.5 with dilute hydrochloric acid and stirred for 15 minutes. The precipitated solid is filtered under suction and washed with acetone. This 3-[[(5-methyl-1,3,4-thiadiazol-2-yl)thio]-methyl]-7-amino-8-oxo-5-thia-1-azabicyclo[4.2.0]oct-2-ene-2-carboxylic acid is purified by dissolving in sodium bicarbonate solution and reprecipitating with 2N hydrochloric acid; yield 12.7 g., m.p. 206°.

EXAMPLE 8

3-[[(3-Methyl-1,2,4-thiadiazol-5-yl)thio]methyl]-7-amino-8-oxo-5-thia-1-azabicyclo[4.2.0]oct-2-ene-2-carboxylic acid By substituting 3-methyl-1,2,4-thiadiazole-5-thiol for the 2-methyl-1,3,4-thiadiazole-5-thiol in the procedure of Example 7, 11.6 g. of 3-[[(3-methyl-1,2,4-thiadiazol-5-yl)thio]methyl]-7-amino-8-oxo-5-thia-1-azabicyclo[4.2.0]oxo-2-ene-2-carboxylic acid, m.p. 186° (dec.) are obtained.

EXAMPLE 9

3-[[(1-Methyl-1H-tetrazol-5-yl)thio]methyl]-7-amino-8-oxo-5-thia-1-azabicyclo[4.2.0]oct-2-ene-2-carboxylic acid By substituting 0.57 M of 1-methyl-1H-tetrazole-5-thiol for the 2-methyl-1,3,4-thiadiazole-5-thiol in the procedure of Example 7, 3-[[(1-methyl-1H-tetrazol-5-yl)thio]-methyl]-7-amino-8-oxo-5-thia-1-azabicyclo[4.2.0]oct-2-ene-2-carboxylic acid is obtained.

EXAMPLE 10

7-Amino-3-[[(5-methyl-1,3,4-thiadiazol-2-yl)thio]methyl]-8-oxo-5-thia-1-azabicyclo[4.2.0]oct-2-ene-2-carboxylic acid, diphenylmethyl ester 18 g. of 7-amino-3-[[(5-methyl-1,3,4-thiadiazol-5-yl)thio]methyl]-8-oxo-5-thia-1-azabicyclo[4.2.0]oct-2-ene-2-carboxylic acid are suspended in 350 ml. of tetrahydrofuran. 4.1 ml. of 70% perchloric acid are added dropwise. After 30 minutes, a slightly turbid solution forms. This solution is filtered and to the filtrate is added dropwise with stirring 12 g. of diphenyldiazomethane and 20 ml. of tetrahydrofuran. After 3 hours, the reaction mixture is poured into 2 liters of absolute ether. The solid, light brown precipitate, which is the perchloric acid salt of the desired product, is dried over Kieselgel in a desiccator. To obtain the base, the perchloric acid salt is dissolved in water and treated with the calculated equivalent of potassium bicarbonate. The aqueous solution obtained is extracted with chloroform. The chloroform phase is treated with activated carbon and sodium sulfate to obtain the 10 g. of the product, 7-amino-3-[[(5-methyl-1,3,4-thiadiazol-2-yl)thio]methyl]-8-oxo-5-thia-1-azabicyclo[4.2.0]oct-2-ene-2-carboxylic acid, diphenylmethyl ester, as a light brown powder, m.p. 157°–159°. The product is recrystallized from tetrahydrofuran/petroleum ether.

EXAMPLE 11

7-Amino-3-[[(1-methyl-1H-tetrazol-5-yl)thio]methyl]-8-oxo-5-thia-1-azabicyclo[4.2.0]oct-2-ene-carboxylic acid, diphenylmethyl ester The product, 7-amino-3-[[(1-methyl-1H-tetrazol-5-yl)thio]methyl]-8-oxo-5-thia-1-azabicyclo[4.2.0]oct-2-ene-carboxylic acid, diphenylmethyl ester, m.p. 168°–169° (dec.), is obtained by the procedure of Example 10 utilizing as starting material 7-amino-3[[(1-methyl-1H-tetrazol-5-yl)thio]-methyl]-8-oxo-5-thia-1-azabicyclo[4.2.0]oct-2-ene-carboxylic acid.

EXAMPLE 12

7β-[[[[(Methylamino)carbonyl]thio]phenylacetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester 1.15 g. of DL-[[(methylamino)carbonyl]thio]-phenylacetic acid and 1 g. (5 mol.) of dicyclohexylcarbodiimide are stirred in 50 ml. of tetrahydrofuran at a temperature of 0°–5°. After 10 minutes a solution of 2.5 g. (5 mol.) of 3-[[(1-methyl-1H-tetrazol-5-yl)thio]methyl]-7-amino-8-oxo-5-thia-1-azabicyclo[4.2.0]oct-2-ene-carboxylic acid diphenylmethyl ester is added dropwise. The whole is stirred for 12 hours, filtered from the dicyclohexylurea formed and after drawing off the solvent, 2.8 g. of the product, 7β-[[[(methylamino)carbonyl]thio]phenylacetyl]amino]-3-[[(1-methyl-1H-tetrazol-5-yl)thio]methyl]-8-oxo-5-thia-1-azabicyclo[4.2.0]oct-2-ene-2-carboxylic aicd, diphenylmethyl ester are obtained. Recrystallization from chloroform/carbon tetrachloride yields a beige powder, m.p. 122°–124° (dec.).

EXAMPLE 13

7β-[[[[(Methylamino)carbonyl]thio]phenylacetyl]amino]-3-[[(1-methyl-1H-tetrazol-5-yl)thio]methyl]-8-oxo-5-thia-1-azabicyclo[4.2.0]oct-2-ene-2-carboxylic acid 2 g. of the product of Example 1 are stirred for 10 minutes at 5° in a mixture of 20 ml. of trifluoroacetic acid and 5 ml. of anisole. After drawing off the trifluoroacetic acid, the mixture is washed with ether/petroleum ether (1:1) and the brown powder obtained is added to a solution of sodium bicarbonate. The whole is filtered, treated with charcoal, cooled at 5° and acidified with 2N hydrochloric acid at pH 2.5. After extraction with ethyl acetate and drawing off of the solvent, the free acid, 7β-[[[[(methylamino)carbonyl]thio]-phenylacetyl]amino]-3-[[(1-methyl-1H-tetrazol-5-yl)thio]methyl]-8-oxo-5-thia-1-azabicyclo[4.2.0]oct-2-ene-carboxylic acid, in the form of a beige powder, is obtained from the organic phase, m.p. 139° (dec.). The product is recrystallized from tetrahydrofuran/petroleum ether.

EXAMPLE 14

7β-[[[[(Methylamino)carbonyl]thio]phenylacetyl]amino]-3-[[(1-methyl-1H-tetrazol-5-yl)thio]methyl]-8-oxo-5-thia-1-azabicyclo[4.2.0]oct-2-ene-2-carboxylic acid, potassium salt The potassium salt is obtained by freeze drying a molecularly equivalent aqueous solution of the acid obtained in Example 2 and potassium bicarbonate as a light colored powder, m.p. 164° (dec.).

EXAMPLES 15 – 49

The products below are obtained by the procedure of Example 12 by reacting the acid

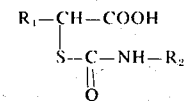

$$R_1-CH-COOH$$
$$|$$
$$S-C-NH-R_2$$
$$\|$$
$$O$$

with the diphenylmethyl ester of one of the following (prepared as in Example 10) and then proceeding according to Example 13 (also Example 14 to obtain a salt):

3-[[(5-methyl-1,3,4-thiadiazolyl-2-yl)thio]-methyl]-7-amino-8-oxo-5-thia-1-azabicyclo[4.2.0]-oct-2-ene-2-carboxylic acid.
3-[[(1-methyl-1H-tetrazol-5-yl)thio]methyl]-7-ACA
3-[[(3-isothiazolyl)thio]methyl]-7-ACA
3-[[(1,3,4-oxadiazol-2-yl)thio]methyl]-7-ACA
3-[[(5-ethyl-1,3,4-oxadiazol-2-yl)thio]methyl]-7-ACA
3-[[(1,2,3,4-tetrazol-5-yl)thio]methyl]-7-ACA
3-[[(1-ethyl-1H-tetrazol-5-yl)thio]methyl]-7-ACA
3-[[(3-methyl-5-isothiazolyl)thio]methyl]-7-ACA
3-[[(3-isothiazolyl)thio]methyl]-7-ACA
3-[[(3-isoxazolyl)thio]methyl]-7-ACA
3-[[(5-methyl-3-isoxazolyl)thio]methyl]-7-ACA
3-[[(1,2,4-thiadiazol-3-yl)thio]methyl]-7-ACA
3-[[(5-butyl-1,2,4-thiadiazol-3-yl)thio]methyl]-7-ACA
3-[[(5-ethyl-3-isoxazolyl)thio]methyl]-7-ACA
3-[[(3-methyl-4-isoxazolyl)thio]methyl]-7-ACA
3-[[(3-methyl-1,2,4-oxadiazol-5-yl)thio]methyl]-7-ACA
3-[[(5-ethyl-3-isothiazolyl)thio]methyl]-7-ACA
3-[[(2-methyl-1,3,4-thiadiazol-5-yl)thio]methyl]-7-ACA
3-[[(1,2,4-thiadiazol-5-yl)thio]methyl]-7-ACA
3-[[(5-methyl-1,3,4-thiadiazol-2-yl)thio]methyl]-7-ACA
3-[[(3-methyl-1,2,4-thiadiazol-5-yl)thio]methyl]-7-ACA
3-[[(1-methyl-1H-tetrazol-5-yl)thio]methyl]-7-ACA
3-[[(1-oxo-2-pyridyl)thio]methyl]-7-ACA

| Example | |
|---|---|
| 15 | 7β-[[[2-(methylamino)carbonyl]thio]-2-(2-pyridyl)acetyl]amino]-3-[[(1,3,4-thiazol-2-yl)thio]methyl]-8-oxo-5-thia-1-azabicyclo[4.2.0]oct-2-ene-2-carboxylic acid |
| 16 | 7β-[[[2-(n-butylamino)carbonyl]thio]-2-phenylacetyl]amino]-3-[[(1,3,4-oxadiazol-2-yl)thio]methyl]-8-oxo-5-thia-1-azabicyclo[4.2.0]oct-2-ene-2-carboxylic acid |
| 17 | 7β-[[[2-(ethylamino)carbonyl]thio]-2-propionyl]amino]-3-[[(5-ethyl-1,3,4-oxadiazol-2-yl)thio]methyl]-8-oxo-5-thia-1-azabicyclo[4.2.0]oct-2-ene-2-carboxylic acid |
| 18 | 7β-[[[2-(benzylamino)carbonyl]thio]acetyl]amino]-3-[[(3-methyl-5-isothiazolyl)thio]methyl]-8-oxo-5-thia-1-azabicyclo[4.2.0]oct-2-ene-2-carboxylic acid |
| 19 | 7β-[[[(2-phenethyl)amino][carbonyl]thio]-2-(2-thienyl)acetyl]amino]-3-[[(3-isothiazolyl)thio]methyl]-8-oxo-5- |

-continued 20  7β-[[[2-(methylamino)carbonyl]thio]-2-phenylacetyl]amino]-3-[[(3-isoxazolyl)thio]methyl]-8-oxo-5-thia-1-azabicyclo[4.2.0]oct-2-ene-2-carboxylic acid
21  7β-[[[2-(methylamino)carbonyl]thio]-2-phenylacetyl]amino]-3-[[(5-methyl-3-isoxazolyl)thio]methyl]-8-oxo-5-thia-1-azabicyclo[4.2.0]oct-2-ene-2-carboxylic acid
22  7β-[[[2-(propylamino)carbonyl]thio]-2-phenylacetyl]amino]-3-[[(1,2,4-thiadiazol-5-yl)thio]methyl]-8-oxo-5-thia-1-azabicyclo[4.2.0]oct-2-ene-2-carboxylic acid
23  7β-[[[2-(methylamino)carbonyl]thio]acetyl]amino]-3-[[(1,2,4-thiadiazol-3-yl)thio]methyl]-8-oxo-5-thia-1-azabicyclo[4.2.0]oct-2-ene-2-carboxylic acid
24  7β-[[[2-(ethylamino)carbonyl]thio]-2-phenylacetyl]amino]-3-[[(5-butyl-1,2,4-thiadiazol-3-yl)thio]methyl]-8-oxo-5-thia-1-azabicyclo[4.2.0]oct-2-ene-2-carboxylic acid
25  7β-[[2-(methylamino)carbonyl]thio]butyramido]-3-[[(1,2,3,4-tetrazol-5-yl)thio]methyl]-8-oxo-5-thia-1-azabicyclo[4.2.0]oct-2-ene-2-carboxylic acid
26  7β-[[(2-methylamino)carbonyl]thio]propionamido]-3-[[(5-methyl-3-isothiazolyl)thio]methyl]-8-oxo-5-thia-1-azabicyclo[4.2.0]oct-2-ene-2-carboxylic acid
27  7β-[[[2-(methylamino)carbonyl]thio]-2-phenylacetyl]amino]-3-[[(3-isoxazolyl)thio]methyl]-8-oxo-5-thia-1-azabicyclo[4.3.0]oct-2-ene-2-carboxylic acid
28  7β-[[[2-(butylamino)carbonyl]thio]acetyl]amino-3-[[(3-methyl-4-isoxazolyl)thio]methyl]-8-oxo-5-thia-1-azabicyclo[4.2.0]oct-2-ene-2-carboxylic acid
29  7β-[[[2-(methylamino)carbonyl]thio]-2-phenylacetyl]amino]-3-[[(3-methyl-1,2,4-oxadiazol-5-yl)thio]methyl]-8-oxo-5-thia-1-azabicyclo[4.2.0]oct-2-ene-2-carboxylic acid
30  7β-[[[2-(methylamino)carbonyl]thio]acetyl]amino]-3-[[(1-ethyl-1H-tetrazol-5-yl)thio]methyl]-1-azabicyclo[4.2.0]oct-2-ene-2-carboxylic acid
31  7β-[[[2-(methoxy)carbonyl]thio]-2-(2-pyridyl)acetyl]amino]-3-[[(1-ethyl-1H-tetrazol-5-yl)thio]methyl]-8-oxo-5-thia-1-azabicyclo[4.2.0]oct-2-ene-2-carboxylic acid
32  7β-[[[2-(ethylamino)carbonyl]thio]-2-(2-pyridyl)acetyl]amino]-3-[[3-thiazolyl]thio]methyl]-8-oxo-5-thia-1-azabicyclo[4.2.0]oct-2-ene-2-carboxylic acid
33  7β-[[[2-(benzylamino)carbonyl]thio]-2-(2-furyl)acetyl]amino]-3-[[(2-methyl-1,3,4-thiadiazol-5-yl)thio]methyl]-8-oxo-5-thia-1-azabicyclo[4.2.0]oct-2-ene-2-carboxylic acid
34  7β-[[[2-(ethylamino)carbonyl]thio]-2-(2-furyl)acetyl]amino]-3-[[(5-methyl-1,3,4-thiadiazol-2-yl)thio]methyl]-8-oxo-5-thia-1-azabicyclo[4.2.0]oct-2-ene-2-carboxylic acid and potassium salt
35  7β-[[2-(propylamino)carbonyl]thio]-2-(2-thienyl)acetyl]amino]-3-[[(1,3,4-oxadiazol-2-yl)thio]methyl]-8-oxo-5-thia-1-azabicyclo[4.2.0]oct-2-ene-2-carboxylic acid and sodium salt
36  7β-[[[(2-phenylethyl)carbonyl]thio]acetyl]amino]-3-[[(5-ethyl-1,3,4-oxadiazol-2-yl)thio]methyl]-8-oxo-5-thia-1-azabicyclo[4.2.0]oct-2-ene-2-carboxylic acid
37  7β-[[[2-(n-butylamino)carbonyl]thio]-2-(2-pyridyl)acetyl]amino-3-[[(1,2,3,4-tetrazol-5-yl)thio]methyl]-8-oxo-5-thia-1-azabicyclo[4.2.0]oct-2-ene-2-carboxylic acid
38  7β-[[[2-(methylamino)carbonyl]thio]-2-(3-thienyl)acetyl]amino]-3-[[(2-methylthiazol-5-yl)thio]methyl-8-oxo-5-thia-1-azabicyclo[4.2.0]oct-2-ene-2-carboxylic acid triethylamine salt
39  7β-[[[[2-(ethylamino)carbonyl]thio]-2-(3-furyl)acetyl]amino]-3-[[(1,2,4-thiadiazol-3-yl)thio]methyl]-8-oxo-5-thia-1-azabicyclo[4.2.0]oct-2-ene-2-carboxylic acid pivaloyloxymethyl ester
40  7β-[[[[2-(methylamino)carbonyl]thio]-2-(3-pyridyl)acetyl]amino]-3-[[(3-isoxazolyl)thio]methyl]-8-oxo-5-thia-1-azabicyclo[4.2.0]oct-2-ene-2-carboxylic acid trimethylsilyl ester
41  7β-[[[[2-(methylamino)carbonyl]thio]-2-(2-thienyl)acetyl]amino]-3-[[(1,3,4-oxadiazol-2-yl)thio]methyl]-8-oxo-5-thia-1-azabicyclo[4.2.0]oct-2-ene-2-carboxylic acid
42  7β-[[[2-(ethylamino)carbonyl]thio]-2-(2-pyridyl)acetyl]amino]-3-[[(5-methyl-1,3,4-thiadiazol-2-yl)thio]methyl]-8-oxo-5-thia-1-azabicyclo[4.2.0]oct-2-ene-2-carboxylic acid diphenylmethyl ester
43  7β-[[[2-(benzylamino)carbonyl]thio]-2-(2-thienyl)acetyl]amino]-3-[[(3-methyl-1,2,4-thiadiazol-5-yl)thio]methyl]-8-oxo-5-thia-1-azabicyclo[4.2.0]oct-2-ene-2-carboxylic acid
44  7β-[[[2-(ethylamino)carbonyl]thio]-2-phenylacetyl]amino]-3-[[(1-methyl-1H-tetrazol-5-yl)thio]methyl]-8-oxo-5-thia-1-azabicyclo[4.2.0]oct-2-ene-2-carboxylic acid
45  7β-[[2-(benzylamino)carbonyl]thio]-2-(2-thienyl)acetyl]amino]-3-[[(1-methyl-1H-tetrazol-5-yl)thio]methyl]-8-oxo-5-thia-1-azabicyclo[4.2.0]oct-2-ene-2-carboxylic acid
46  7β-[[[2-methylamino)carbonyl]thio]-2-(2-pyridyl)acetyl]amino]-3-[[(1-methyl-1H-tetrazol-5-yl)thio]methyl]-8-oxo-5-thia-1-azabicyclo[4.2.0]oct-2-ene-2-carboxylic acid
47  7β-[[[2-(benzylamino)carbonyl]thio]-2-(2-furyl)acetyl]amino]-3-[[(1-methyl-1H-tetrazol-5-yl)thio]methyl]-8-oxo-5-thia-1-azabicyclo[4.2.0]oct-2-ene-2-carboxylic acid
48  7β-[[[2-(methylamino)carbonyl]thio]phenylacetyl]amino]-3-[[(1-oxo-2-pyridyl)thio]methyl]-8-oxo-5-thia-1-azabicyclo[4.2.0]oct-2-ene-2-carboxylic acid
49  7β-[[[[(methylamino)carbonyl]thio]phenylacetyl]amino]-3-[[(5-methyl-1,3,4-thiadiazol-2-yl)thio]methyl]-8-oxo-5-thia-1-azabicyclo[4.2.0]oct-2-ene-2-carboxylic acid and potassium salt

What is claimed is:
1. A compound of the formula

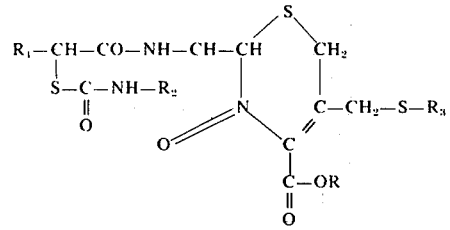

wherein R is hydrogen, lower alkyl, phenyl-lower alkyl, diphenylmethyl, tri(lower alkyl)silyl,

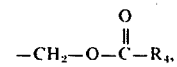

alkali metal, alkaline earth metal, mono (lower alkyl) amine salt or tri (lower alkyl) amine salt; $R_1$ is hydrogen, lower alkyl, phenyl, thienyl, furyl or pyridyl; $R_2$ is lower alkyl, phenyl-lower alkyl or diphenyl methyl; $R_3$ is $R_5$-thiadiazole, $R_5$-oxadiazole, $R_5$-isoxazole, $R_5$-isothiazole, $R_5$-tetrazole or $R_5$-pyridine-N-Oxide; $R_4$ is lower alkyl, phenyl, phenyl-lower alkyl or diphenyl methyl; and $R_5$ is hydrogen or lower alkyl; said lower alkyl groups having up to seven carbon atoms.

2. A compound as in claim 1 wherein $R_1$ is phenyl.
3. A compound as in claim 2 wherein $R_2$ is lower alkyl.
4. A compound as in claim 1 wherein R is hydrogen, alkali metal, trimethylsilyl, diphenylmethyl or

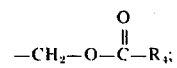

$R_1$ is phenyl or thienyl; $R_2$ is lower alkyl; $R_3$ is (lower alkyl)tetrazole or (lower alkyl)thiadiazole; and $R_4$ is methyl or t-butyl.

5. A compound as in claim 2 wherein R is hydrogen and $R_2$ is lower alkyl.
6. A compound as in claim 4 wherein R is hydrogen, $R_1$ is phenyl, $R_2$ is lower alkyl and $R_3$ is (lower alkyl)tetrazole.
7. A compound as in claim 4 wherein R is alkali metal, $R_1$ is phenyl, $R_2$ is lower alkyl and $R_3$ is (lower alkyl)-tetrazole.
8. A compound as in claim 4 wherein R is hydrogen, $R_1$ is phenyl, $R_2$ is methyl and $R_3$ is 1-methyl-1H-tetrazol-5-yl.
9. Alkali metal salt of the compound of claim 8.
10. Diphenylmethyl ester of the compound of claim 8.
11. A compound as in claim 1 wherein $R_1$ is thienyl.

* * * * *